(12) United States Patent
Beaume

(10) Patent No.: US 7,746,458 B2
(45) Date of Patent: Jun. 29, 2010

(54) DIAGNOSING OR DETERMINING PARAMETERS FOR AN INSTALLATION FOR DETECTING OPEN DEFECTS IN THE SURFACES OF PARTS BY SWEATING

(75) Inventor: Pascal Didier Beaume, Bayonne (FR)

(73) Assignee: Turbomeca, Bordes (FR)

( * ) Notice: Subject to any disclaimer, the term of this patent is extended or adjusted under 35 U.S.C. 154(b) by 304 days.

(21) Appl. No.: 11/553,258

(22) Filed: Oct. 26, 2006

(65) Prior Publication Data

US 2007/0097360 A1 May 3, 2007

(30) Foreign Application Priority Data

Oct. 28, 2005 (FR) ................................. 05 11045

(51) Int. Cl.
*G01N 21/00* (2006.01)
(52) U.S. Cl. .................................. 356/237.1
(58) Field of Classification Search ................ 356/237, 356/249, 239.1
See application file for complete search history.

(56) References Cited

U.S. PATENT DOCUMENTS

| 5,539,656 | A | * | 7/1996 | Annigeri et al. | 702/35 |
| 5,563,417 | A | * | 10/1996 | Gillard et al. | 250/461.1 |
| 5,570,431 | A | * | 10/1996 | Gillard et al. | 382/149 |
| 5,673,203 | A | * | 9/1997 | Annigeri et al. | 702/42 |
| 6,097,484 | A | * | 8/2000 | McIntosh et al. | 356/237.5 |
| 6,465,801 | B1 | * | 10/2002 | Gann et al. | 250/559.4 |
| 6,690,460 | B2 | * | 2/2004 | Chiu et al. | 356/239.1 |
| 7,271,894 | B2 | * | 9/2007 | Devitt et al. | 356/241.1 |
| 7,355,193 | B2 | * | 4/2008 | Gann et al. | 250/559.45 |

FOREIGN PATENT DOCUMENTS

| EP | 0 650 045 A1 | 4/1995 |
| WO | WO 91/07654 | 5/1991 |
| WO | WO 97/02484 | 1/1997 |

OTHER PUBLICATIONS

H.J. Stumm, "Detection of surface cracks by means of penetrating agents" Git Fachzeitschrift Fuer Das Laboratorium, Darmstadt, Germany, ISSN: 0016-3538, XP000600361, vol. 17, No. 9, 1973, pp. 955, 957-958.

* cited by examiner

*Primary Examiner*—Tarifur R. Chowdhury
*Assistant Examiner*—Isiaka O Akanbi
(74) *Attorney, Agent, or Firm*—Oblon, Spivak, McClelland, Maier & Neustadt, L.L.P.

(57) ABSTRACT

A method of diagnosing or determining parameters for an installation for detecting open defects in the surfaces of parts by sweating, the method including passing at least one standard testpiece through the installation, the testpiece having a surface possessing at least one pattern representative of the type of defect that is to be detected, applying to the surface of the testpiece a penetrating composition including an indicator substance, washing, drying, applying to the surface of the testpiece a composition including a developer, and illuminating the surface of the testpiece to illuminate any remaining indicator substance so as to form a developed image of the or each pattern and deduce therefrom an indication about the quality of the operation of the installation. Prior to passing through the installation, the standard testpiece is subjected to preparatory treatment including immersion in a bath containing an emulsifier, a first rinse under pressure, drying, applying a developer at the location(s) of the pattern(s), and a second rinse under pressure.

12 Claims, 2 Drawing Sheets

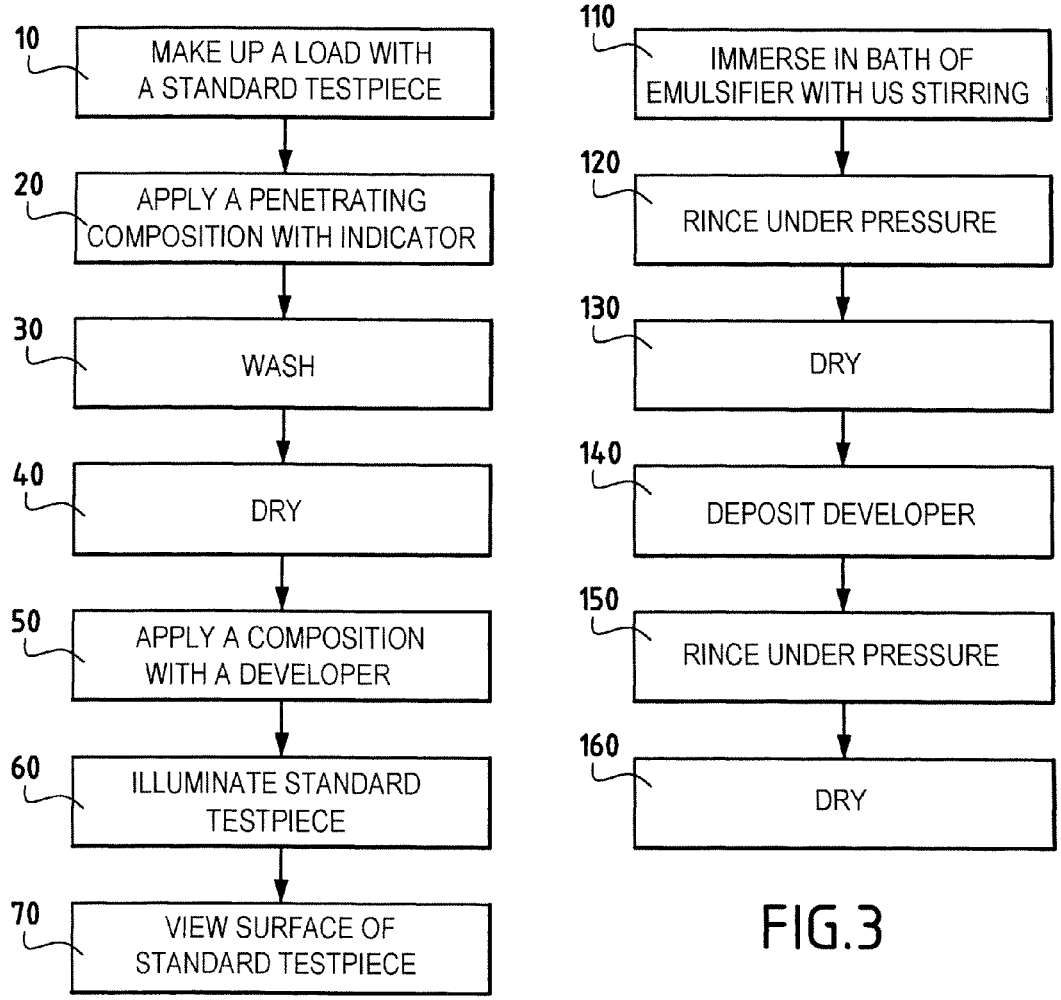
FIG.1
FIG.3
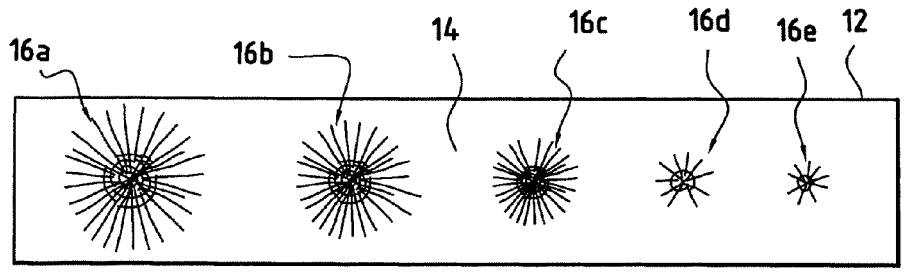
FIG.2

DIAGNOSING OR DETERMINING PARAMETERS FOR AN INSTALLATION FOR DETECTING OPEN DEFECTS IN THE SURFACES OF PARTS BY SWEATING

BACKGROUND OF THE INVENTION

The invention relates to diagnosing or determining parameters for installations for detecting open defects in the surfaces of parts, in particular metal parts, by using the sweating technique.

Sweating is a well-known technique for non-destructive testing of parts that might present open surface defects, such as cracks or fissures, for example. A penetrating composition containing a detector or indicator substance is applied to the surface of the part to be inspected. The detector or indicator substance typically comprises a colored or fluorescent compound that shines when exposed to appropriate light. After the penetrating composition has been applied, the surface of the part is washed so as to be cleaned, and then it is dried. A composition containing an absorbent substance or developer is then deposited on the surface of the part. By capillarity, the developer causes any indicator substance that has penetrated into open defects to return to the surface (where it is "sweated out"). Illuminating the surface by light appropriate for the indicator substance, typically ultraviolet (UV) light, serves to show up any defects, thus enabling the part to be inspected by visual examination.

A description of known methods of detecting surface fissures using penetrating substances can be found in the article by H. J. Stumm entitled "Der Nachweis von Oberflachenrissen mit Hilfe von Eindringmitteln", G-I-T Fachzeitschrift für das Laboratorium, Darmstadt, DE, Vol. 17, No. 9, 1973, pp. 955, 957-958.

The quality of detection is sensitive to numerous installation set-up parameters and it is necessary to undertake regular verification that the installation is operating properly. For this purpose, use is made of standard testpieces that have a surface presenting patterns that are representative of the types of open defect that are to be detected. The standard testpiece, optionally together with a batch of parts for inspection, is caused to pass through the installation and the patterns developed at the end of the sweating process on the surface of the standard testpiece are verified for compliance with the patterns whose geometrical characteristics are already known.

Standard testpieces can be used not only for verifying proper operation of an installation for detecting defects by sweating, but also for determining the parameters of such an installation, i.e. for optimizing the settings of the various parameters that have an influence on the quality of detection, as proposed in patent document EP 0 650 045.

OBJECT AND SUMMARY OF THE INVENTION

The Applicant has found that the diagnoses of installations performed using standard testpieces in the usual way are not necessarily always reliable, and seeks to provide a method of diagnosing or determining parameters for an installation for detecting defects by sweating in which the results observed on a standard testpiece after it has passed through the installation are guaranteed to be a true reflection of the quality of the detection performed by the installation.

This object is achieved by a method comprising passing at least one standard testpiece through an installation for inspection, the testpiece having a surface presenting at least one pattern representative of the type of defect to be detected, applying to the surface of the testpiece a penetrating composition including an indicator substance, washing, drying, applying to the surface of the testpiece a composition that includes a developer, and illuminating the surface of the testpiece in order to illuminate any remaining indicator substance so as to form a developed image of the or each pattern and deduce therefrom an indication about the quality of the operation of the installation, in which method, prior to being passed through the installation, the standard testpiece is subjected to preparatory treatment comprising immersion in a bath containing an emulsifier, a first rinse under pressure, drying, applying a developer at least at the location of the or each pattern, and a second rinse under pressure.

The Applicant has found that in the absence of such a cleaning process for preparing a standard testpiece, it can happen that the various substances used during the sweating process, in particular the indicator substance and the developer, can accumulate in the patterns of the standard testpiece, progressively clogging them up with increasing number of uses of the standard testpiece. Consequently, persisting presence of the indicator substance in the patterns means that they will necessarily show up when developed at the end of sweating, even if the real quality of the detection process has become degraded. It is then possible to reach an entirely detrimental situation in which the patterns of the standard testpiece appear to be properly developed, while real defects in the parts going through the installation are not developed at all.

The standard testpiece is preferably immersed in a bath containing an emulsifier while also applying ultrasound energy. It is also preferable for the surface of the standard testpiece that has the patterns to be inclined relative to a horizontal plane in said bath.

During preparatory treatment of the standard testpiece, the application of the developer to the locations of the patterns serves to extract a mixture of penetrating composition, emulsifier, and developer that might still be present in the patterns before eliminating by rinsing under pressure. It is possible to use a developer in the liquid state that can easily be applied by being sprayed on the form of an aerosol.

According to a feature of the invention, an image of the illuminated standard testpiece is digitized by a camera for transmission to a digital processor unit provided with a display screen, the image being digitized after being filtered by means of a filter centered on the wavelength of the radiation emitted by the indicator substance. This serves to eliminate any possible influence of interfering radiation. By displaying the image on the screen, or by processing the image digitally, it is possible to deduce from the image as obtained, information representative of the geometrical characteristics of the developed pattern, in particular its area and its maximum dimension, and information representative of the mean gray level of a developed image of a pattern. Analyzing this information can serve to direct a search looking for causes of incomplete or erroneous detection of patterns in order to diagnose malfunction of the installation, or it can be used to optimize values for the operating parameters of an installation.

BRIEF DESCRIPTION OF THE DRAWINGS

Other features and advantages of the present invention appear on reading the following description given by way of non-limiting indication and with reference to the accompanying drawings, in which:

FIG. 1 shows the successive steps in a diagnostic method using an installation for detecting surface defects by sweating;

FIG. 2 is a diagrammatic view of an example of a standard testpiece used in the method of FIG. 1;

FIG. 3 shows the successive steps of a process for preparing the standard testpiece in order to implement the method of FIG. 1;

DETAILED DESCRIPTION OF IMPLEMENTATIONS OF THE INVENTION

Figure 4:
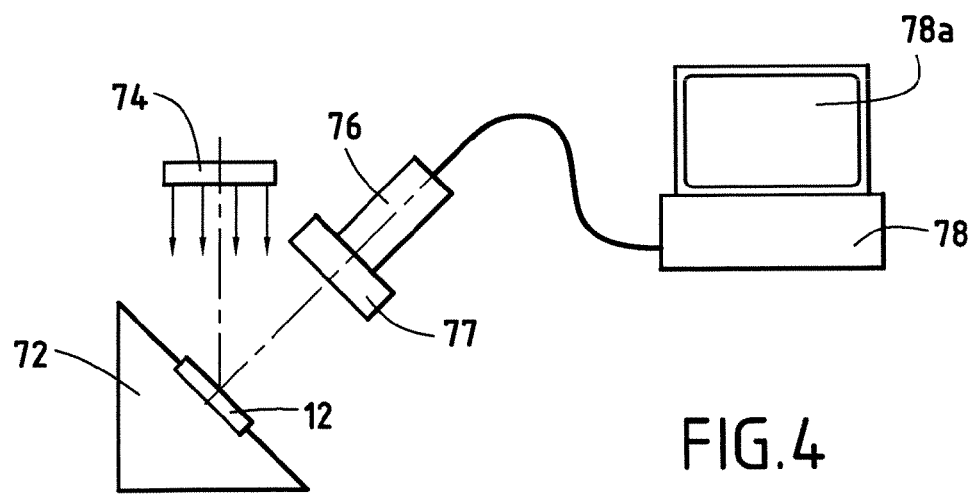
FIG. 4 is a diagram showing apparatus for acquiring an image of the surface of the standard testpiece after passing through an installation for detecting defects.

FIG. 1 shows the successive steps in a method of diagnosing or inspecting an installation for using a sweating technique to detect any defects that open out into the surfaces of parts, which method consists in causing at least one standard testpiece to pass through the installation under inspection while subjecting the standard testpiece to treatments that are identical to those applied to the parts on whose surfaces any defects are to be detected.

In well-known manner, a standard testpiece is used having a surface that presents one or more patterns that are representative of the types of open defects that are to be detected in the surfaces of metal parts, such as fissures and cracks. An example of such a standard testpiece 12 is sold by the supplier Babb Co under the reference "PSM5" and is shown diagrammatically in FIG. 2. A main surface 14 of the testpiece presents a plurality of patterns, specifically five patterns 16a to 16e of decreasing sizes. In this example, each pattern is generally in the form of a star, in particular with fissures radiating from a central zone and of varying width. Naturally, the method of the invention is not limited to using this particular type of standard testpiece and pattern.

An installation for detecting defects by sweating is diagnosed on a regular basis, e.g. daily or after a certain number of loads of parts for inspection have been passed through, possibly by associating a standard testpiece with a load of parts for inspection. Thus, step 10 of the method of FIG. 1 consists in making up a load that includes a standard testpiece as well as parts for inspection. Naturally, it would also be possible to use a plurality of standard testpieces, and it would also be possible not to include any parts for inspection with the standard testpiece(s).

The load is placed in a vessel in which a penetrating composition including a detector or indicator substance is applied by being sprayed onto the surface of the standard testpiece and the part (step 20). The indicator substance is typically a colored or fluorescent substance that shines under UV radiation of appropriate characteristics. It is common practice to use a compound which, when illuminated with UV radiation having a wavelength of about 365 nanometers (nm), shines brightly by producing radiation at a wavelength of about 550 nm. Such a compound of sensitivity "W3" or "P3" and known as a pre-emulsioned or post-emulsioned penetrant is well known.

Washing (step 30) is subsequently performed to clean the surfaces of the standard testpiece and of the parts. Washing can be performed in a plurality of steps while using an emulsifying agent that serves to eliminate the composition containing the indicator substance from the surfaces of the standard testpiece and of the parts. Thus, it is possible to perform in succession pre-rinsing by spraying water under pressure, immersion in a stirred bath of emulsifying agent, and rinsing by spraying water under pressure. Washing could be limited to a single step of rinsing using water under pressure, in particular when an emulsifying agent is incorporated in the indicator substance.

After drying in hot air (step 40), a composition containing a developer is deposited on the surfaces of the standard testpiece and of the parts, at least on the surface of the standard testpiece that presents the patterns and on the surfaces of the parts where any open defects are to be detected (step 50). A developer is used that is capable, by capillarity, of sweating out the indicator substance that has penetrated into the patterns in the standard testpiece and into any defects in the parts. It is common practice to use a powder (and in particular talc) that has grains that are very fine, with the capacity of extracting by capillarity the penetrating composition that has penetrated into any open defects in the parts for inspection, and into the patterns of the standard testpiece, and the powder is deposited as a uniform layer.

The surface of the standard testpiece that has the patterns and that is coated in the developer is illuminated by a source of UV light that matches the indicator substance used (step 60). Zones where the indicator substance is present then shine brightly, and viewing the surface of the standard testpiece (step 70). makes it possible to verify whether the patterns therein are properly developed by comparing the developed images with their known real geometrical characteristics. The result of the test can be considered as being positive so long as the difference between the dimensions of the developed images of the patterns and the real dimensions thereof remain within predetermined limits.

It is advantageous to perform step 70 of viewing the surface of the standard testpiece by using an image that is displayed on a display screen. At least certain checks can then be undertaken in automated manner by processing a digitized image produced by a camera.

Equipment for analyzing images produced by illuminating a standard testpiece after it has passed through a detector installation is shown in FIG. 4. The testpiece 12 is placed on a support 72 with its face 14 directed outwards. A source 74 producing UV radiation appropriate for illuminating the indicator substance absorbed by the developer is caused to emit towards the testpiece 12 along a direction of incidence that makes a non-zero angle relative to the normal to the surface 14. By way of example, the source 74 is a source of UV radiation having a wavelength of about 365 nm.

Figure 5:
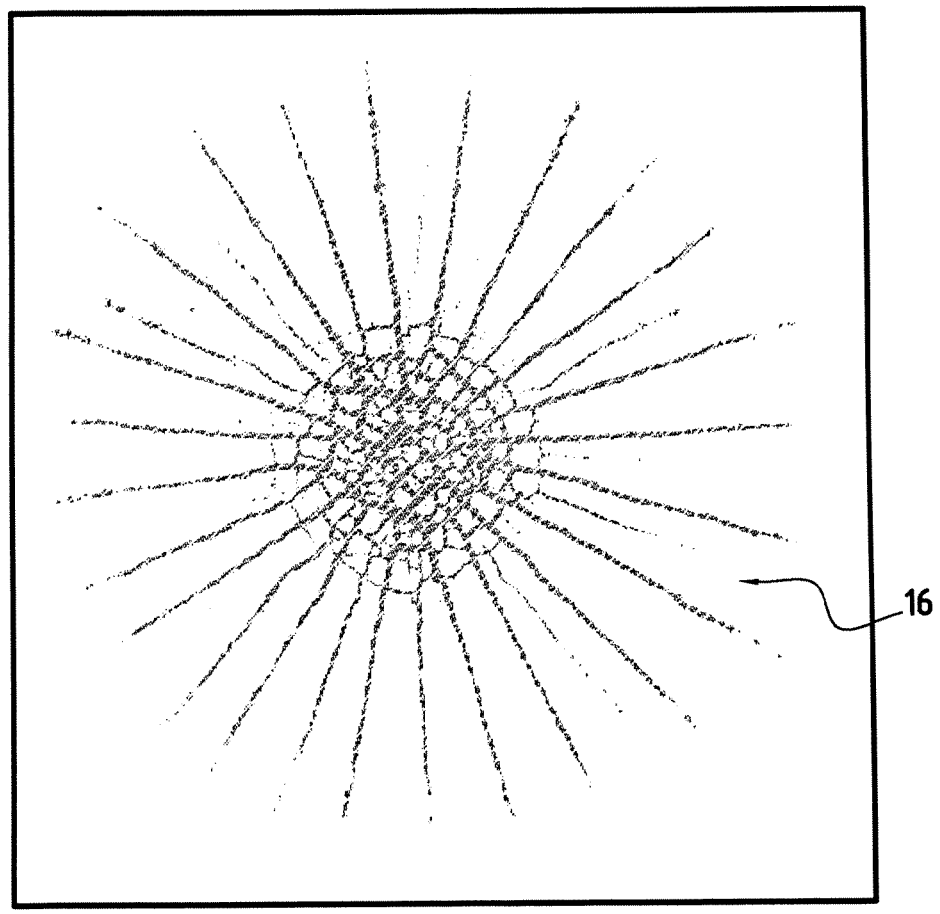
FIG. 5 shows an image of a pattern developed on the standard testpiece, as acquired by the FIG. 4 device.

An image of the surface 14 is taken by a camera 76, and the resulting digital information is transmitted to a digital processor unit such as a personal computer 78 having a screen 78a on which the image can be viewed. FIG. 5 shows an example of an image of a pattern as developed by the sweating process and as displayed on the screen 78a.

A filter 77 centered on the wavelength re-emitted by the indicator is placed in front of the lens in order to eliminate interfering light. In the above-mentioned example of an indicator substance emitting at a wavelength of 550 nm, it is possible to use a filter that allows practically only that wavelength to pass through, i.e. a filter having a very narrow passband.

Various kinds of information characteristic of the developed image of one or more patterns can be obtained by viewing the screen or by automatic processing. Thus:

viewing can be performed to detect any discontinuities in the fissures of the patterns or to detect the presence of any excess sweating in the form of clumping or smudging, making it possible to diagnose that the amount of indicator substance used was insufficient or excessive;

information representing the total area occupied by the developed image of one or each pattern can be calculated, giving an indication concerning the quality of the sweating and enabling comparisons to be performed from one inspection to another;

information representing the maximum dimension of one or each pattern can be calculated and compared with the known real maximum dimension of the pattern, e.g. in order to determine an acceptability threshold; and information representing the mean gray level of a pattern or of each pattern can also be calculated, and can provide an indication about the quality of the indicator substance, and in particular its capacity for emitting light.

Other information that is useful for verifying proper operation of the installation can be obtained from the image taken of the surface of the standard testpiece.

As mentioned above, the Applicant has found that the diagnostic method can cease to be reliable after the standard testpiece has been used a certain number of times. The reason that has been identified lies in the patterns becoming partially clogged by a mixture of the various substances used during the process, including the indicator substance. The persistence of indicator substance remaining present means that the patterns in which it remains will necessarily be developed even in the event of the installation operating poorly, and that naturally completely falsifies the diagnosis made concerning the installation.

FIG. 3 shows the successive steps of a process of preparing the standard testpiece that enables the above drawbacks to be avoided.

A first step 110 consists in immersing the standard testpiece in a bath containing an emulsifier. The immersion is preferably performed in a vessel coupled to an ultrasound generator so as to perform stirring using ultrasonic energy that helps eliminate the indicator substance. The emulsifier is selected as a function of the indicator substance used. It is preferable to keep the face of the standard testpiece with the patterns in a position that is inclined relative to a horizontal plane, e.g. inclined at an angle of about 45°, so as to enhance the action of the emulsifier. Immersion together with the application of ultrasound energy is performed over a duration that is preferably longer than 30 minutes (min), e.g. lying in the range 30 min to several hours.

After rinsing in water under pressure (step 120) and drying by blowing air under pressure (step 130), a developer is applied to the surface of the testpiece that presents the patterns, or at least to the locations of the patterns (step 140). Advantageously, a wet developer is used that is sprayed on in the form of an aerosol, in order to be effective in comparison with a developer in the form of a dry powder. After the applied developer has been dried, it performs its function of extracting any indicator substance that might still be present.

After rinsing in water under pressure (step 150) and drying by blowing air under pressure (step 160), a standard testpiece is obtained ready for use having patterns that are free from the presence of any residue of the indicator substance.

The method of the invention can be implemented not only for diagnosing an installation, but also for optimizing the settings of certain parameters of the sweating process, by implementing a process of the type described in patent document EP 0 650 045. By way of example, such parameters can be the duration and the pressure of spraying the composition containing the indicator substance, the pressure of the rinsing and possibly also pre-rinsing water, and the duration and the pressure with which the developer is sprayed.

Parameters can be determined for use when starting a new installation or when using a new indicator substance or developer, and the method of the invention can subsequently be used periodically for diagnosing or inspecting proper operation of the installation.

What is claimed is:

1. A method of diagnosing or determining parameters for an installation for detecting open defects in the surfaces of parts by sweating, the method comprising: providing at least one standard testpiece having a surface possessing at least one pattern having known geometrical characteristics representative of the type of defect that is to be detected; passing the testpiece through the installation to perform the steps of applying to the surface of the testpiece a penetrating composition including an indicator substance, washing the surface of the testpiece, drying, and applying to the surface of the testpiece a composition including a second developer; and illuminating the surface of the testpiece to illuminate the remaining indicator substance so as to form a developed image of the at least one pattern and deduce therefrom an indication about the quality of the operation of the installation by comparing the developed image with said known geometrical characteristics, wherein, prior to passing through the installation, the standard testpiece is subjected to cleaning treatment comprising the steps of: immersing the testpiece in a bath containing an emulsifier with the surface of the testpiece being inclined relative to a horizontal plane; carrying out a first rinsing under pressure drying; applying a first developer at the location of the at least one pattern; and carrying out a second rinse under pressure, in order to eliminate from the at least one pattern any residue of indicator substance accumulated from a previous use of the testpiece, prior to passing the testpiece through the installation for diagnosing or determining parameters for the installation.

2. A method according to claim 1, wherein the standard testpiece is immersed in an emulsifyer-containing bath while also applying ultrasound energy.

3. A method according to claim 2, wherein said immersing and said applying are performed for over 30 minutes.

4. A method according to claim 2, wherein said immersing and said applying are performed for several hours.

5. A method according to claim 1, wherein, during the preparatory treatment of the standard testpiece, the first developer is applied in the wet state by spraying.

6. A method according to claim 1, wherein information is deduced from the developed image of the or each pattern, which information is taken from at least information representative of the geometrical characteristics and information representative of the mean gray level of the developed image of the pattern.

7. A method according to claim 6, wherein information is deduced representative of the area and of the maximum size of the image of the pattern.

8. A method according to claim 6, wherein the developed image of the surface of the standard testpiece is digitized by a camera for transmission to a digital processor unit provided with a display screen, after filtering by means of a filter centered on the wavelength of the radiation emitted by the indicator substance.

9. A method according to claim 1, wherein the first and second developers are different from each other.

10. A method according to claim 9, wherein the first developer is a wet spray and the second developer is a dry powder.

11. A method according to claim 1, wherein said step of illuminating the surface of the testpiece is performed by illuminating the surface with UV light matching the indicator substance.

12. A method according to claim 11, wherein the method is free of any step of illuminating the testpiece with UV light between applying the first developer and applying the second developer.

* * * * *